United States Patent [19]

Cortese, Jr. et al.

[11] Patent Number: 5,371,229
[45] Date of Patent: Dec. 6, 1994

[54] METHOD FOR THE PREPARATION OF 2,3-PYRIDINE-DICARBOXYLIC ACIDS AND DERIVATIVES THEREOF

[75] Inventors: Nicholas A. Cortese, Jr., Mercerville; Henry L. Strong, Somerset, both of N.J.

[73] Assignee: American Cyanamid Company, Wayne, N.J.

[21] Appl. No.: 967,350

[22] Filed: Oct. 28, 1992

[51] Int. Cl.$^5$ .............. C07D 213/803; C07D 213/807
[52] U.S. Cl. .................................. 546/320; 546/319; 546/250
[58] Field of Search .................. 546/250, 319, 320

[56] References Cited

U.S. PATENT DOCUMENTS

| | | | |
|---|---|---|---|
| 3,342,792 | 9/1967 | Toekelt | 526/91 |
| 4,097,492 | 6/1978 | Rohrscheid | 549/232 |
| 4,798,619 | 1/1989 | Los | 504/156 |

OTHER PUBLICATIONS

Organic Chemistry (N.Y.), 5 (C):295–342; 1978.
ACS Symposium Series, 22:156–159; 1978.
Chemistry and Industry, 250-251; 1961.
Metal–Catalyzed Oxidations of Organic Compounds, R. A. Sheldon and J. K. Kochi (Academic Press: New York, N.Y.) 1981.

*Primary Examiner*—Alan L. Rotman
*Attorney, Agent, or Firm*—John W. Hogan, Jr.

[57] ABSTRACT

There is provided an improved process for the preparation of substituted and unsubstituted 2,3-pyridinedicarboxylic acids in significantly enhanced yield by the nitric acid oxidation of the appropriately substituted quinoline precursor in the presence of a catalytic amount of Manganese.

10 Claims, No Drawings

METHOD FOR THE PREPARATION OF 2,3-PYRIDINE-DICARBOXYLIC ACIDS AND DERIVATIVES THEREOF

BACKGROUND OF THE INVENTION

Substituted and unsubstituted 2,3-pyridinedicarboxylic acids are important intermediates in the manufacture of highly active 2-(2-imidazolin-2-yl)nicotinate herbicides. Literature methods to prepare said pyridinedicarboxylic acids include nitric acid oxidation of the appropriately substituted quinoline precursor. Most prominent in the literature describing nitric acid oxidations are those methods which employ nitric acid alone or in the presence of Vanadium salts. However, these procedures generally give unsatisfactory yields and undesirable by-products when used to convert quinoline derivatives to the corresponding pyridinedicarboxylic acid compounds.

It is an object of this invention to provide an improved nitric acid oxidation of quinoline derivatives to their corresponding pyridinedicarboxylic acid compounds. Another object of this invention is to provide a convenient and efficient source of an important herbicidal intermediate. These and further objects of the invention will become apparent in the detailed description below.

SUMMARY OF THE INVENTION

The present invention provides an improved process for the manufacture of 2,3-pyridinedicarboxylic acid compounds of formula I

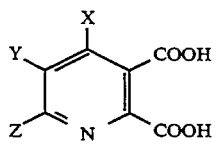

wherein X is hydrogen or methyl with the proviso that when Y and Z are taken together to form a ring, X is hydrogen;

Y and Z are each independently hydrogen, $C_1$-$C_6$alkyl optionally substituted with one or more $C_1$-$C_4$alkoxy, halogen, sulfonyl or $R_1R_2N$ groups, nitro, $C_1$-$C_4$alkylcarbonyl, $C_1$-$C_4$alkylsulfonyl, $R_1R_2N$, $R_1R_2NSO_2$, or phenyl optionally substituted with one or more $C_1$-$C_4$alkyl, $C_1$-$C_4$alkylsulfonyl, halogen, or haloalkyl groups, and when taken together Y and Z may form a ring wherein YZ is represented by the structure —$(CH_2)$—$_n$ or

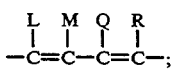

$R_1$ and $R_2$ are each independently hydrogen or $C_1$-$C_4$alkyl;

n is an integer of 3 or 4 and

L, M, Q and R are each independently hydrogen, $C_1$-$C_4$alkyl, $C_1$-$C_4$alkoxy, $C_1$-$C_4$alkylsulfonyl, $C_1$-$C_4$haloalkyl, nitro, $R_1R_2N$, phenyl optionally substituted with one $C_1$-$C_4$alkyl or halogen group or phenoxy optionally substituted with one halogen, $C_1$-$C_4$alkyl, nitro or $CF_3$ group with the proviso that only one of L, M, Q or R may represent a substituent other than hydrogen, halogen, $C_1$-$C_4$alkyl or $C_1$-$C_4$alkoxy, which comprises reacting a compound of formula II

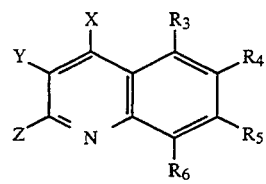

wherein X, Y and Z are as described above for formula I and $R_3$, $R_4$, $R_5$ and $R_6$ are each independently hydrogen, hydroxy, nitro, amino, $SO_3H$ or $SO_3Cl$ with the proviso that one of $R_3$, $R_4$, $R_5$ or $R_6$ is other than hydrogen; the N-oxides thereof and the acid addition salts thereof with nitric acid in the presence of a catalytic amount of Manganese, optionally in the presence of a solvent, at an elevated temperature.

The formula I pyridinedicarboxylic acids are useful as intermediates in the production of 2-(2-imidazolin-2-yl)nicotinate herbicidal agents. Descriptions of said herbicidal agents and the use of formula I intermediates in their preparation can be found in U.S. Pat. No. 4,798,619 among others.

DETAILED DESCRIPTION OF THE INVENTION

Formula I pyridinedicarboxylic acid compounds are commercially important intermediates in the field of agriculture, unfortunately, literature methods for their preparation are limited. It has now been found, that the addition of a catalytic amount of Manganese with a valence of $Mn^{+2}$ through $Mn^{+7}$ to the nitric acid oxidation of an appropriate quinoline precursor of formula II gives a significant increase in reaction yield and a decrease of undesirable by-products.

Formula II starting 8-substituted-quinolines may be readily prepared by procedures known in the art such as the Skraup reaction, Doebner-Miller reaction or the sulfonation of quinoline.

In actual practice, a formula II quinoline compound, optionally dissolved in a suitable solvent, is added to a mixture of 70% nitric acid and a catalytic amount of Manganese at a temperature range of about 50°-150° C., the reaction mixture is heated at 50°-150° C. until the product formation is complete. The resultant reaction mixture may be quenched by the addition of a reducing agent such as formic acid, formaldehyde, isopropyl alcohol, acetone, and the like. The desired formula I product may be isolated using standard procedures known in the art such as precipitation and filtration, extraction with a suitable solvent, chromatographic separation and the like. The reaction is shown in flow diagram I.

FLOW DIAGRAM I

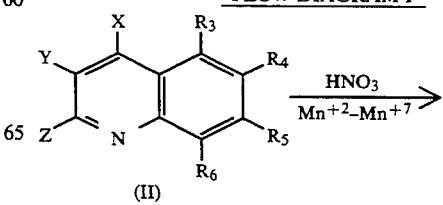

-continued
FLOW DIAGRAM I

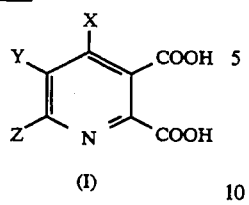

(I)

Solvents suitable for use in the method of invention may be those which are water immiscible and unreactive under acid oxidation conditions. In general, halogenated hydrocarbons such as methylene chloride, ethylene dichloride, chlorobenzene, dichlorobenzene and the like are suitable. Managanese sources may be any of the oxides or salts wherein manganese is present in a valence state of +2 to +7, preferably $MnO_2$ or $KMnO_4$.

The reaction rate is directly proportional to the reaction temperature, therefore increased reaction temperatures correspond to shortened reaction times. However, exceedingly high reaction temperatures may lead to decomposition products or side reactions, thereby diminishing the desired product yield. Suitable reaction temperatures are about 50°–150° C., preferably about 85°–110° C.

The method of the invention is further illustrated by the following non-limiting examples.

EXAMPLE 1

Evaluation of the Nitric Acid Oxidation of 3-methyl-8-hydroxyquinoline in the Absence of a Manganese Catalyst

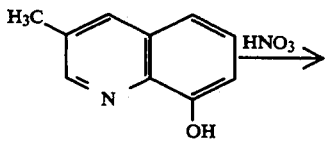

A) A solution of 3-methyl-8-hydroxyquinoline (15.9 g, 0.10 mole) in methylene chloride is added to 70% nitric acid (126 g, 1.8 mole) at a temperature of 80°–100° C. over a 1 hour period with stirring. The resulting overhead gases are scrubbed and vented. The reaction mixture is heated at 100°–105° for 4 hours, cooled to 85° C., treated with 88% formic acid at 85°–95° C. over a 20 minute period, further heated at 85°–95° C. for 0.5 hour, cooled to 0°, stirred for 1 hour and filtered. The filtercake is washed with acetone and dried to give 5-methyl-2,3-pyridinedicarboxylic acid, 10.6 g (58.6% yield), 97.4% pure by HPLC analysis.

B) Using essentially the same procedure and employing 2.6 mole nitric acid, 5-methyl-2,3-pyridinedicarboxylic acid is obtained 10.7 g (59.1% yield), 98% purity by HPLC analysis.

EXAMPLE 2

Evaluation of Nitric Acid Oxidation of 3-methyl-8-hydroxyquinoline in the Presence of a Manganese Catalyst

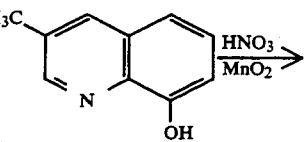

A) A solution of 3-methyl-8-hydroxyquinoline (15.9 g, 0.10 mole) is added to a mixture of 70% nitric acid (162 g, 1.8 mole) (18 molar equivalents) and Manganese dioxide (0.33 g, 0.0038 mole) (0.038 molar equivalents) at a temperature of 80°–100° C. over a 1 hour period, with stirring. The resultant overhead gases are scrubbed and vented. The reaction mixture is heated at 100°–105° C. for 4 hours, cooled to 85° C., treated with 88% formic acid at 85°–95° C. over a 20 minute period, further heated at 85°–95° C. for 0.5 hour, cooled to 0° C., stirred for 0.5 hour and filtered. The filtercake is washed with acetone to give 5-methyl-2,3-pyridinedicarboxylic acid, 13.6 g (78.3% yield), 98.8% purity by HPLC analysis.

B) Using essentially the same procedure and decreasing the amount of nitric acid to 15.6 molar equivalents, 5-methyl-2,3-pyridinedicarboxylic acid is obtained in 78.6% yield and 98% purity.

C) Using procedure A described above and reducing the amount of Manganese dioxide employed to 0.005 molar equivalents, 5-methyl-2,3-pyridinedicarboxylic acid is obtained in 73.2% yield and 98.5% purity.

EXAMPLE 3

Evaluation of the Nitric Acid Oxidation of 3-ethyl-8-hydroxyquinoline With and Without the Presence of Manganese

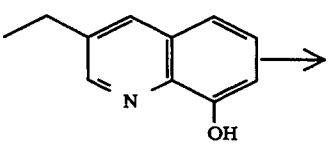

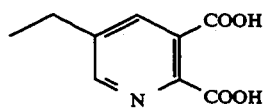

General Procedure

A 20% solution of 3-ethyl-8-hydroxyquinoline in methylene chloride is added to 70% nitric acid (27–43 molar equivalents) containing 0–0.063 molar equivalents of Manganese at 80°–100° C. over a 1 hour period, with stirring. The resultant overhead gases are scrubbed and vented. The reaction mixture is heated at 100°–105° C. for 4 hours, cooled to room temperature and assayed by HPLC to determine the amount of 5-ethyl-2,3- pyridinedicarboxylic acid present. The results are shown in Table I.

TABLE I

| | Effect Of Catalytic Manganese On The Yield Of Nitric Acid Oxidation of 3-Ethyl-8-hydroxyquinoline | | | | | | | | |
|---|---|---|---|---|---|---|---|---|---|
| | Starting Material | | Nitric Acid | | | Manganese | | | Product |
| Reaction | wt. | moles | wt. | moles | Molar equiv. | Source | wt. | moles | Molar equiv. | % yield |
| A | 52.5 g | 0.303 | 1170 g | 13.0 | 43.3 | — | 0 | 0 | 0 | 66.57 |
| B | 5.25 g | 0.030 | 82 g | 0.91 | 30.3 | — | 0 | 0 | 0 | 68.08 |
| C | 10.72 g | 0.062 | 164 g | 1.82 | 29.3 | — | 0 | 0 | 0 | 68.53 |
| D | 5.25 g | 0.030 | 82 g | 0.91 | 30.3 | $KMnO_4$ | 0.3 g | 0.0019 | 0.063 | 87.59 |
| E | 10.72 g | 0.062 | 164 g | 1.82 | 29.3 | $MnO_2$ | 0.2 g | 0.0023 | 0.039 | 93.24 |
| F | 10.72 g | 0.062 | 164 g | 1.82 | 29.3 | $MnO_2$ | 0.3 g | 0.0035 | 0.056 | 98.52 |
| G | 25.24 g | 0.146 | 360 g | 4.00 | 27.4 | $MnO_2$ | 0.75 g | 0.0086 | 0.058 | 94.55 |

What is claimed is:

1. A process for the preparation of a compound of formula I

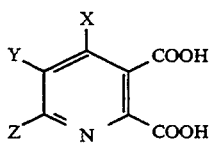
(I)

wherein X is hydrogen or methyl;

Y and Z are each independently hydrogen, $C_1$–$C_6$alkyl optionally substituted with one or more $C_1$–$C_4$alkoxy, halogen, sulfonyl or $R_1R_2N$ groups, nitro, $C_1$–$C_4$alkylcarbonyl, $C_1$–$C_4$alkylsulfonyl, $R_1R_2N$, $R_1R_2NSO_2$, or phenyl optionally substituted with one or more $C_1$–$C_4$alkyl, $C_1$–$C_4$alkylsulfonyl, halogen, or haloalkyl groups, $R_1$ and $R_2$ are each independently hydrogen or $C_1$–$C_4$alkyl;

which comprises reacting a compound of formula II

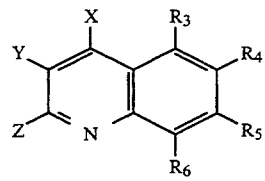
(II)

wherein X, Y and Z are as described for formula I above and $R_3$, $R_4$, $R_5$ and $R_6$ are each independently hydrogen, hydroxy, nitro, amino, $SO_3H$ or $SO_3Cl$ with the proviso that at least one of $R_3$, $R_4$, $R_5$ or $R_6$ is other than hydrogen; the N-oxides thereof or the acid addition salts thereof with nitric acid in the presence of a catalytically effective amount of Manganese, optionally in the presence of a solvent, at an elevated temperature.

2. The process according to claim 1 wherein the Manganese is present as $KMnO_4$ or $MnO_2$.

3. The process according to claim 1 wherein the temperature is about 50°–150°.

4. The process according to claim 1 wherein a solvent is present.

5. The process according to claim 4 wherein the solvent is a halogenated hydrocarbon.

6. The process according to claim 1 wherein Y is hydrogen or $C_1$–$C_4$alkyl and X and Z are hydrogen.

7. The process according to claim 6 wherein $R_6$ is hydroxy and $R_3$, $R_4$ and $R_5$ are hydrogen.

8. The process according to claim 1 wherein the formula I compound is 2,3-pyridinedicarboxylic acid.

9. The process according to claim 1 wherein the formula I compound is 5-methyl-2,3-pyridinedicarboxylic acid.

10. The process according to claim 1 wherein the formula I compound is 5-ethyl-2,3-pyridinedicarboxylic acid.

* * * * *